United States Patent

Wulfsberg

[11] Patent Number: 5,842,972
[45] Date of Patent: Dec. 1, 1998

[54] ENDOSCOPE OPTICS

[75] Inventor: Jens Peter Wulfsberg, Ammersbek, Germany

[73] Assignee: Olympus Winter & Ibe GmbH, Hamburg, Germany

[21] Appl. No.: 896,215

[22] Filed: Jul. 17, 1997

[30] Foreign Application Priority Data

Aug. 7, 1996 [DE] Germany .................. 196 31 840.8

[51] Int. Cl.$^6$ ........................................ A61B 1/04
[52] U.S. Cl. .................. 600/167; 600/168; 600/170; 600/173; 600/133
[58] Field of Search ............................. 600/133, 146, 600/167, 168, 170, 173

[56] References Cited

U.S. PATENT DOCUMENTS

| | | | |
|---|---|---|---|
| 3,525,331 | 8/1970 | Mori | 600/167 |
| 4,341,205 | 7/1982 | Hosono et al. | 600/133 |
| 4,832,473 | 5/1989 | Ueda | 600/167 |
| 4,846,155 | 7/1989 | Kimura | 600/167 |
| 4,905,668 | 3/1990 | Ohsawa | 600/167 |
| 4,982,725 | 1/1991 | Hibino et al. | 600/146 |
| 5,188,094 | 2/1993 | Adair | 600/133 |
| 5,634,881 | 6/1997 | Francis | 600/133 |

Primary Examiner—Richard J. Apley
Assistant Examiner—Ira Hatton
Attorney, Agent, or Firm—Walter C. Farley

[57] ABSTRACT

An endoscope optics has a rigid and substantially tubular housing containing several optical components, the housing being sealed against entry into the housing of steam or water vapor from the ambient housing atmosphere. At least one of the optical components is displaceable. The housing has at least one deformable wall segment such as a membrane or bellows which, when deformed, drives an adjustment member engaging the displaceable optical component and adjusts the position of the optical component within the housing.

5 Claims, 1 Drawing Sheet

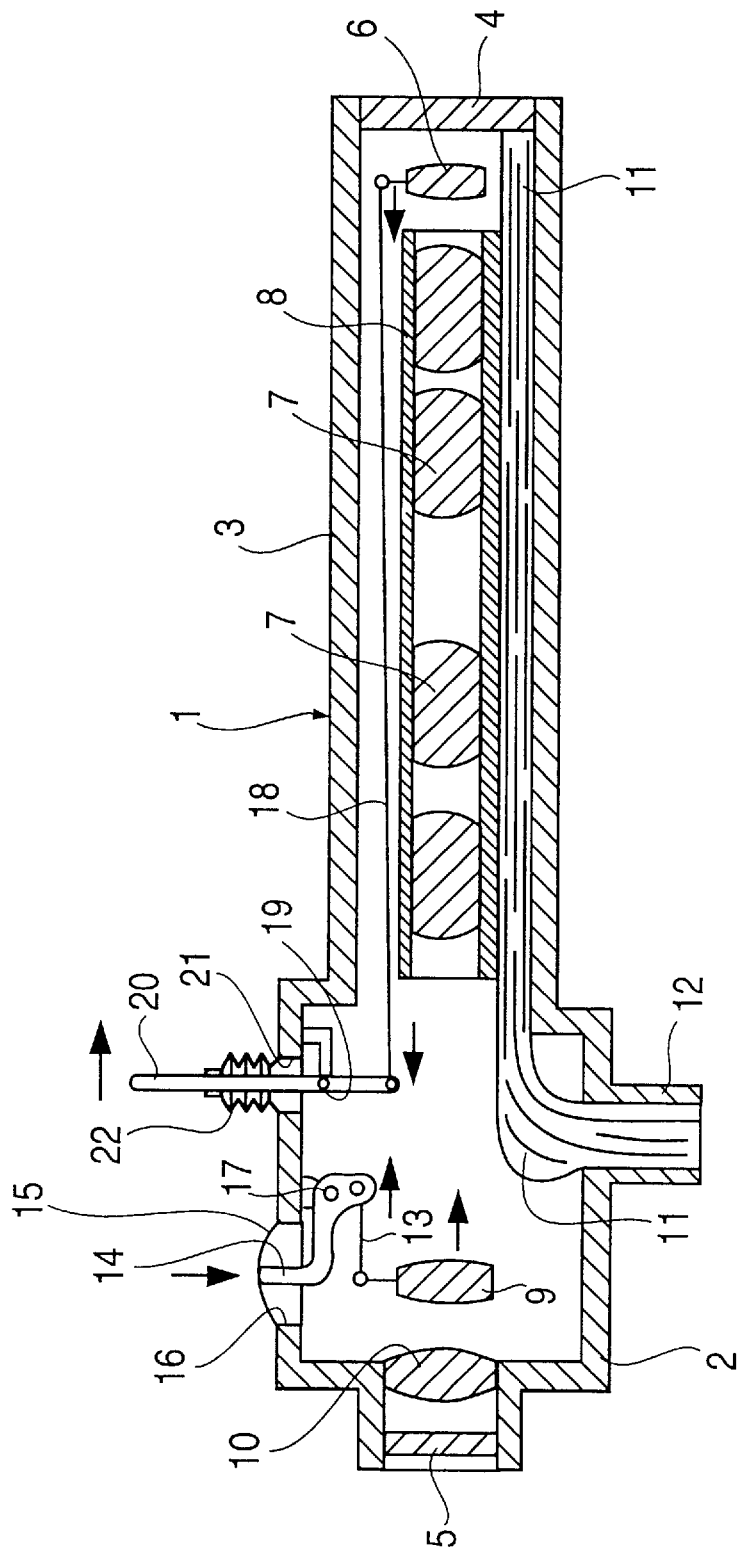

ENDOSCOPE OPTICS

FIELD OF THE INVENTION

The invention concerns a rigid endoscope optical system with a tubular, vapor-tight housing and optical components including at least one movable component and a deformable wall segment for driving the movable component.

BACKGROUND OF THE INVENTION

Endoscope optics are usually mounted either rigidly attached to an endoscope or they are designed with a distally elongated shank portion telescoping into a matching channel of the endoscope.

Endoscope optics of this type contain a series of optical components, in particular lenses etc., by which they transmit an image produced in the distal optics zone to the proximal end where it may then be viewed. As a rule, an objective is mounted for that purpose in the distal end zone of the endoscope optics. The transmission to the proximal end of the endoscope is implemented by an image guide, for instance in the form of a series of bar lenses that stretches longitudinally through the endoscope. However, the image guide also may be fiber optics. The proximal viewing system, for instance, may be a video camera hooked up to, or mounted in, the endoscope optics, or an ocular.

Endoscope optics must be sterilized before intervention. Present-day requirements on sterilization are met by autoclaving in steam at about 140° C. To preclude the steam from entering the endoscope optics where it may deposit as droplets or dew on the lens surfaces, the endoscope optics must be sealed off as much as possible. In general, therefore, the housings of such optics are made as integral as possible in metal form. In zones precluding integral design, for instance in the region of the viewing windows present at the distal and at the proximal ends, these windows must be bonded or soldered into place using the latest techniques.

A problem arises because, after their manufacture, no inside retrofitting is possible in such sealed optics. Consequently, all lens elements already must be accurately adjusted and affixed at manufacture. Therefore, the manufacture of such conventional endoscope optics is fairly expensive.

U.S. Pat. No. 5,056,902 discloses a focusing system which can be connected to the proximal end of an arthroscope optics and which has a steam-tight housing containing an adjustable lens. The lens adjustment is implemented by a variable magnetic field. It is questionable whether such a magnetic adjusting system also may be used in the actual endoscope optics. Complexity appears substantial.

SUMMARY OF THE INVENTION

Accordingly, it is an object of the present invention to create a well-sealed endoscope optics of simple design wherein at least one of the optic elements is adjustable in order to adjust and/or to vary the optical properties.

This object is achieved by an endoscope optics having, in accordance with the present invention, at least one displaceable optic components present in the steam-tight housing of the endoscope optics. The adjustment of the displaceable optic component, for instance to adjust the endoscope optics, but also optionally to change the angle of view or the focal length if so desired, is implemented mechanically. More specifically, the endoscope optics housing, depending on the number of displaceable optical components, comprises one or more deformable wall segments which, when deformed, drives an adjustment member inside the housing and engages the displaceable optical component.

The expression "deformable wall segments" is to be construed broadly. Illustratively, it also includes displaceable wall segments which per se are not deformable but are joined to deformable wall segments.

The deformable wall segments may be constructed in a number of ways. Conceivably the housing may have a limited wall segment that is extremely thin in the manner of a depressible membrane. Illustratively, a spring-loaded free end of an adjusting lever may rest against the inside of that wall segment. When the wall segment is pressed inward, and is appropriately positioned relative to and connected, for instance, to one optic component, this component may be axially displaced within the endoscope optics. Equally feasible are adjustments by rotation or, if so desired, by radial displacement. If a distal optical component is to be displaced by the deformable wall segment which is preferably located in the proximal end zone of the endoscope optics, then a push and pull rod can easily ensure corresponding transmission.

Another possible design for a deformable wall segment is a portion of the housing, for instance, in the form of an outwardly projecting metal bellows. In its conventional form, that is with peripheral troughs, such a bellows when suitably driven at its outer free sealing surfaces offers various adjusting features. Thus, it may be pressed inward uniformly. Just as well, the sealing surface may be stressed only unilaterally and in the process an inside and rigidly affixed lever may be pivoted.

However, a helical bellows might also be used to provide rotation, for instance.

In theory, the two above arrangements allow deformable wall the segment by direct finger contact. However, grip means alternatively may be attached to the deformable wall segments to implement the desired deformation. A substantial advantage of such grip means is that, after depressing a deformable wall segment, the latter can be easily pulled back into its initial position. In this respect, return springs may also be used which, especially with respect to the first approach, also may compensate for wall indenting forces.

In addition, and with respect to the various possible arrangements, the adjusted position of the optical component can be fixed in place easily by an outer fixation device such as a detent by means of which the deformable wall segment or a grip means attached to it can be fixed in various positions.

The invention is not restricted to the above mentioned wall segments but also covers arrangements not cited as long as they allow adequate wall segment deformation to adjust an optic component.

The main advantage of the invention is that it allows in simple manner transmission of mechanical adjusting forces into a perfectly sealed endoscope optics housing. As a result, it is possible to manufacture autoclavable endoscope optics which are initially coarsely adjusted and to fine control the adjustment thereafter. Just as well, the autoclavable endoscope optics may be fitted with adjustable directions of viewing or with adjustable focal lengths.

BRIEF DESCRIPTION OF THE DRAWINGS

The invention is described below with reference to a drawing which is a side elevation, in longitudinal section, of an embodiment of an endoscope optics or optical system in accordance with the invention.

DESCRIPTION OF THE PREFERRED EMBODIMENTS

The figure shows an endoscope optics comprising a housing 1 having a proximal end zone 2 attached to a distal tubular shank 3. Windows 4 and 5, respectively, are mounted in and close the distal end of the shank 3 and the proximal end of the housing zone 2. The windows 4 and 5 illustratively are special-soldered to the housing in such a way that optimal sealing of the inner space of the housing 1 is assured even when autoclaving is undergone repeatedly. In the best state of the present art, the windows 4 and 5 are metallized at their outer edges and are soldered to the housing when this metal layer is incorporated.

The optical components of the endoscope optics include an objective lens 6 mounted in the distal region of the housing, an image transmission system 8 including several elongated bar lenses 7, a zoom lens 9 and an ocular lens 10. One or more optical fibers 11 are provided to illuminate the surveyed region to be imaged by the objective 6 and extend from a proximal optical-fiber terminal 12 to distal window 4.

Two different embodiments of lens adjusting mechanisms of the invention will be discussed with reference to the drawing. The above-mentioned zoom lens 9 is displaceably supported in a slide guide, not shown, in the direction of arrow 24, that is, axially. Lens 9 is linked to a rod 13 connected in articulating manner to the inner end of a bellcrank lever 14. The other end of bellcrank lever 14 rests against a metal membrane 15 soldered into an aperture 16 in a side wall of housing 2. When membrane 15 is depressed in the direction of arrow 25, then the upper end of bellcrank lever 14 is forced downwardly. In the process, bellcrank lever 14 is pivoted about a bearing 17 and carries rod 13 in the direction of arrow 26, thereby also axially displacing the zoom lens.

A second embodiment relates to displacing the objective lens 6. Lens 6 is connected in articulating manner to a push/pull rod 18 essentially extending along and through tubular housing shank 3. Rod 18 is supported at its proximal end at the inside end of a lever 20 which is pivotally supported at 19 in housing portion 2. Lever 20 passes outwardly through an aperture 21 in housing portion 2. The lower inside edge of a metal bellows 22 is soldered to aperture 21 and the outer end is soldered to lever 20. The solder seal is selected in both cases such that absolute steam and water vapor tightness is assured. When the outer end of the lever 20 is displaced in the direction of arrow 27, push/pull rod 18 is displaced toward the proximal end of the housing 1 and carries with it objective 6 which is slidingly supported in a slide guide, not shown. As already mentioned, adjusting screws or detent mechanisms may be outside the seal to engage, for instance, membrane 15 or lever 20 and to allow accurate adjustment of the lenses driven by the particular mechanism. Moreover, springs may be used to automatically return the deformable wall segments to their initial positions. It will also be apparent that displacement of lever 20 made possible by bellows 22 is not restricted to the displacements discussed above. Using cooperating adjustment members, it is also easy to depress the lever to different levels into the housing, as already mentioned.

What is claimed is:

1. An endoscope optics comprising
   a rigid and substantially tubular housing (1) having an interior volume;
   a plurality of optical components in said housing interior, at least one said optical component (6, 9) being displaceable within said housing;
   means for steam-tight sealing said housing interior against the ambient atmosphere;
   said housing (1) comprising at least one deformable wall segment (15, 22); and
   an adjusting member (18, 13) inside said housing (1) coupled to said deformable wall segment and to said displaceable optical component (6, 9) whereby movement of said deformable wall segment displaces said displaceable optical component.

2. An endoscope optics according to claim 1, and including a lever (20) attached to said wall segment (22) to deform said segment.

3. An endoscope optics according to claim 2 wherein said deformable wall segment is a bellows (15).

4. An endoscope optics according to claim 1 wherein said deformable wall segment is a flexible membrane (15).

5. An endoscope optics according to claim 4 and including a pivotable lever in said interior volume responsive to movement of said membrane to displace said displaceable optical component.

\* \* \* \* \*